United States Patent
Mond et al.

(10) Patent No.: US 6,432,679 B1
(45) Date of Patent: *Aug. 13, 2002

(54) ENHANCEMENT OF B CELL ACTIVATION AND IMMUNOGLOBULIN SECRETION BY CO-STIMULATION OF RECEPTORS FOR ANTIGEN AND EBV GP350/220

(75) Inventors: James J. Mond; Andrew Lees, both of Silver Spring, MD (US)

(73) Assignee: Henry M. Jackson Foundation for the Advancement of Military Medicine, Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/328,599

(22) Filed: Jun. 10, 1999

Related U.S. Application Data

(60) Provisional application No. 60/089,158, filed on Jun. 12, 1998.

(51) Int. Cl.$^7$ .......................... C12P 21/04; C12N 15/00; C12N 5/06; A61K 45/00

(52) U.S. Cl. .................. 435/69.7; 435/334; 435/320.1; 424/199.1; 424/230.1; 424/186.1; 424/192.1; 424/278.1; 530/350; 536/23.72

(58) Field of Search ........................... 424/230.1, 278.1, 424/186.1, 194.1, 192.1; 435/69.7, 334, 320.1; 530/350; 536/23.72

(56) References Cited

U.S. PATENT DOCUMENTS

| | | |
|---|---|---|
| 4,376,110 A | 3/1983 | David et al. |
| 4,486,530 A | 12/1984 | David et al. |
| 4,518,584 A | 5/1985 | Mark et al. |
| 4,737,462 A | 4/1988 | Mark et al. |
| 5,011,912 A | 4/1991 | Hopp et al. |
| 5,280,113 A | 1/1994 | Rademacher et al. |
| 5,310,729 A | 5/1994 | Lernhardt |
| 5,331,090 A | 7/1994 | Lernhardt |
| 5,521,066 A | 5/1996 | Menzel et al. |
| 5,585,100 A | 12/1996 | Mond et al. |
| 5,651,971 A | 7/1997 | Lees |
| 5,693,326 A | 12/1997 | Lees |
| 5,712,149 A | 1/1998 | Roberts |
| 6,054,130 A | 4/2000 | Spaete et al. |

FOREIGN PATENT DOCUMENTS

| | | |
|---|---|---|
| WO | WO 90 04176 | 4/1990 |
| WO | WO 93 19092 | 9/1993 |
| WO | WO 95 28488 | 10/1995 |
| WO | WO 96 17625 | 6/1996 |

OTHER PUBLICATIONS

Goeckeritz et al, Eur. J. Immuno, 2000, vol. 30, pp. 969–973.*

International Search Report for application No. PCT/US 99/13113.

Allison et al., "Induction of IL–5 Receptors On Normal B Cells By Cross–Linking Surface Ig With Anti–Ig–Dextran," *The Journal of Immunology*, vol. 146, No. 12, pp. 4197–4203, Jun. 15, 1991.

Goroff et al., "Activation of B Cells In Vivo By A Fab/Fc Fragment Of A Monoclonal Anti–IgD Antibody Requires An Interaction Between The Antibody Fragment And A Cellular IgG Fc Receptor," *The Journal of Immunology*, vol. 140, pp. 2919–2924, May 1, 1988.

Sieckmann et al., "Activation of Mouse Lymphocytes by Anti–Immunoglobulin," *Cellular Immunology*, vol. 85, pp. 1–14, 1984.

Sieckmann et al., "IgD As A Receptor In Signaling The Proliferation Of Mouse B–Lymphocytes," *Annals of the New York Academy of Sciences*, vol. 399, pp. 277–289, 1982.

Barel et al., "Monoclonal and Anti–Idiotypic Anti–EBV/C3d Receptor Antibodies Detect Two Binding Sites, One for EBV and One for C3d on Glycoprotein 140, the EBV/C3dR, Expressed on Human B Lymphocytes," J. Immunol. 141:1590–1595 (1988).

Barel et al., Isolation and Characterization of A C3b Receptor–Like Molecule from Membranes of a Human B Lymphoblastoid Cell Line (Raji), Febs Letters 136(1):111–114 (1981).

Bauer et al., "A genetic enrichment for mutations constructed by oligodeoxynucleotide–directed mutagenesis," Gene 37:73–81 (1985).

Beisel et al., "Two Major Outer Envelop Glycoproteins of Epstein–Barr Virus Are Encoded by the Same Gene," J. Virol. 54(3):665–674 (1985).

(List continued on next page.)

Primary Examiner—Ali R. Salimi
(74) Attorney, Agent, or Firm—Finnegan, Henderson, Farabow, Garrett & Dunner, LLP

(57) ABSTRACT

The present invention provides vaccine adjuvants comprising the Epstein Barr Virus glycoprotein 350/220 or naturally occurring variants thereof, a fusion protein comprising EBV Gp350/220 sequence which binds to the CR2 receptor, or a synthetically-derived fragment of Gp350/220 which retains the ability to bind to the CR2 receptor. The present invention further provides immunostimulatory compositions comprising an EBV Gp350/220 adjuvant sequence that binds the CR2 complex and at least one antigen of interest other than Gp350/220. Co-administration of the adjuvant with an antigen of interest, other than an antigen comprising EBV 350/220 sequence, enhances the immunogenicitiy of the antigen. In a preferred embodiment, the adjuvant is directly or indirectly covalently bound to an antigen of interest to form an immunogenic composition. In a most preferred embodiment of the composition, antibodies are elicited against at least one Gp350/220 epitope and against at least one epitope of the antigen.

20 Claims, 3 Drawing Sheets

OTHER PUBLICATIONS

Boackle et al., "CD21 augments antien presentation in immune individuals," Eur. J. Immunol. 27:122–120 (1997).

Brinkley, "Brief Survey of Methods for Preparing Protein Conjugates With Dyes, Haptens and Cross–Linking Agents," Bioconjugate Chem., 3:2–13 (Jan. 1992).

Brunswick et al., "Picogram Quantities of Anti–Ig Antibodies Coupled to Dextran Induce B Cell Proliferation," J. Immunol. 140(10):3364–3372 (1988).

Brunswick et al., "Surface immunoglobulin–mediated B–cell activation in the absence of detectable elevations in intracellular ionized calcium: A model for T–cell–independent B–cell activation," Proc. Nat'l. Acad. Sci. USA 86:6724–28 (1989).

Carter et al., "CD19: Lowering the Threshold for Antigen Receptor Stimulation of B Lymphocytes," Science 256:105–107 (1992).

Craik, "Use of Oligonucleotides for Site–Specific Mutagenesis," BioTechniques 12–19 (Jan. 1985).

Croix et al., "Antibody Response to a T–dependent Antigen Requires B Cell Expression of Complement Receptors," J. Exp. Med. 183:1857–1864 (1996).

Delcayre et al., "gp140, the EBV/C3d receptor (CR2) of human B lymphocytes, is involved in cell–free free phosphorylation of p120, a nuclear ribonucleoprotein," Eur. J. Immunol. 17:1827–1833 (1987).

Delcayre et al., "Enhancement of Epstein–Barr Virus/C3d Receptor (EBV/C3dR or CR2) and Nuclear p120 Ribonucleoprotein Phosphorylation by Specific EBV/C3dR Ligands in Subcellular Fractions of the Human B Lymphoma Cell Line, Raji," BBRC 159:1213–20 (1989).

Dempsey et al., "C3d of Complement as a Molecular Adjuvant: Bridging Innate and Acquired Immunity," Science 271:348–50 (1996).

Devereux et al., "A comprehensive set of sequence analysis programs for the VAX," Nucl. Acids Res. 12(1):387–395 (1984).

Dick et al., "Glycoconjugates of Bacterial Carbohydrate Antigens," Conjugate Vaccines, Contrib. Microbiol. Immunol. 10:48–114 (1989).

Finerty et al., "Protective immunization against EpsteinBarr virus–induced disease in cottontop tamarins using the virus envelope glycoprotein gp340 produced from a bovine papillomavirus expression vector," J. Gen. Virol. 73:449–453 (1992).

Fingeroth et al., "Epstein–Barr virus receptor of human B lymphocytes is the C3d receptor CR2," Proc. Natl. Acad. Sci. USA 81:4510–4514 (1984).

Fingeroth et al., "Proliferation of resting B cells in modulated by CR2 and CR1," Immunol. Letters 21:291–302 (1989).

Frade et al., "A 16 Amino Acid Synthetic Peptide Derived from Human C3d Triggers Proliferation and Specific Tyrosine Phosphorylation of Transformed CR2–Positive Human Lymphocytes and of Normal Resting B Lymphocytes," BBRC 188:833–842 (1992).

Frade, "Structure and signalling functions of C3 receptors on human B cells," Seminars in Immunology 2:159–164 (1990).

Frade et al., gp140, a C3b–binding membrane component of lymphocytes, is the B cell C3dg/C3d receptor (CR2) and is distinct from the neutrophil C3dg receptor (CR4), Eur. J. Immunol. 15:1192–1197 (1985).

Frade et al., "Enhancement of human B cell proliferation by an antibody to the C3d receptor, the gp 140 molecule," Eur. J. Immunol. 15:73–76 (1985).

Frade et al., "gp140, the C3d receptor of human B lymphocytes, is also the Epstein–Barr virus receptor," Proc. Natl. Acid. Sci. USA 82:1490–93 (1985).

Gribskov et al., "Sigma factors from *E. coli, B. subtilis*, phage SP01, and phage T4 are homologous proteins," Nucl. Acids Res. 14(16):6745–6763 (1986).

Halista et al., "Characterization of Early Activation of Events in Cord Blood B Cells after Stimulation with T Cell–Independent Activators," Ped. Res. 43(4):496–503 (1998).

Hartmann et al., "Stimulation of Murine B Lymphocytes by Isolated C3b," J. Exp. Med. 142:600–10 (1975).

Hartmann, "Possible Involvement of C3 During Stimulation of B Lymphocytes," Transplant, Rev. 23:98–104 (1975).

Hatzfeld et al., "C3 Stimulates Proliferation of Human Pre–B Raji Cells," Ann. Inst. Pasteur/Immunol. 138:451–455 (1987).

Hermanson, G.T., "Bioconjugate Techniques," Academic Press, San Diego (1996) (detailed contents only).

Hopp et al., "A Short Polypeptide Marker Sequence Useful for Recombinant Protein Identification and Purification," Bio/Technology 6:1204–1210 (1988).

Kozono et al., "Cross–Linking CD21/CD35 or CD19 Increases Both B7–1 and B7–2 Expression on Murine Splenic B Cells," J. Immunol. 160:1565–1572 (1998).

Kunkel, "Rapid and efficient site–specific mutagenesis without phenotypic selection," Proc. Natl. Acad. Sci. USA 82:488–492 (1985).

Kunkel et al., "Rapid and Efficient Site–Specific Mutagenesis without Phenotypic Selection," Methods in Enzymol. 154:367–383 (1987).

Lambris et al., "Mapping of the C3d receptor (CR2)–binding site and a neoantigenic site in the C3d domain of the third component of complement," Proc. Natl. Acad. Sci. USA 82:4235–4239 (1985).

Lees et al., "Enhanced immunogenicity of protein–dextran conjugates: I. Rapid stimulation of enhanced antibody responses to poorly immunogenic molecules," Vaccine 12(13):1160–1166 (1994).

Lees et al., "Rapid Stimulation of Large Specific Antibody Responses with Conjugates of Antigen and Anti–IgD Antibody," J. Immunol. 145(11):3594–3600 (1990).

Lyamani et al., "A 16 Amino–Acid Synthetic Peptide, Derived from Human C3d, Carries Regulatory Activity on In Vitro Phosphorylation of a Cellular Component of the Human B Lymphoma Cells, Raji," BBRC 175(3):823–830 (1991).

Masucci et al., "Activation of B lymphocytes by EpsteinBarr virus/CR2 receptor interaction," Eur. J. Immunol. 17:815–820 (1987).

Melchers et al., "Factors Controlling the B–Cell Cycle," Ann. Rev. Immunol. 4:13–36 (1986).

Melchers et al., "Growth control of activated, synchronized murine B cells by the C3d fragment of human complement," Nature 317:264–267 (1985).

Molina et al., "Markedly impaired humoral immune response in mice deficient in complement receptors 1 and 2," Proc. Natl. Acad. Sci. USA 93:3357–3361 (1996).

Mongini et al., "The Affinity Threshold for Human B Cell Activation Via the Antigen Receptor Complex is Reduced Upon Co–Ligation of the Antigen Receptor with CD21 (CR2)," J. Immunol. 159:3782–3791 (1997).

Monsigny et al., "Colorimetric Determination of Neutral Surgars by a Resorcinol Sulfuric Acid Micromethod," Anal. Chem. 175:525–530 (1988).

Morgan et al., "Recombinant Vaccinia Virus Expressing Epstein–Barr Virus Glycoprotein gp340 Protects Cottontop Tamarins Against EB Virus–Induced Malignant Lymphomas," J. Med. Virol. 25:189–195 (1988).

Morgan, "Epstein–Barr virus vaccines," Vaccine 10:563–571 (1992).

Needleman et al., "A General Method Applicable to the Search for Similarities in the Amino Acid Sequence of Two Proteins," J. Mol. Biol. 48:443–453 (1970).

Nemerow et al., "Binding of Monoclonal Antibody to the Epstein Barr Virus (EBV)/CR2 Receptor Induces Activation and Differentiation of Human B Lymphocytes," J. Immunol. 135:3068–3073 (1985).

Nemerow et al., "Identification of gp350 as the Viral Glycoprotein Mediating Attachment of Epstein–Barr Virus (EBV) to the EBV/C3d Receptor of B Cells: Sequence Homology of gp350 and C3 Complement Fragment C3d," J. Virol. 61(5):1416–1420 (1987).

Paul, Fundamental Immunology, Table of Contents, Chapters 3–5, and Subject Index (1989).

Roit, Essential Immunology, Table of Contents, Chapters 1, 9, and 13, and Subject Index (1994).

Sármay et al., "Integration of activatory and inhibitory signals in human B–cells," Immunol. Letters 54:93–100 (1996).

Sato et al., "Regulation of B Lymphocyte Development and Activation by the CD19/CD21/CD81/Leu 13 Complex Requires the Cytoplasmic Domain of CD19," J. Immunol. 159(7):3278–3287 (1997).

Schwartz et al., "Atlas of Protein Sequence and Structure," National Biomedical Research Foundation 353–58 (1978).

Schenkein et al., "Inhibition of Lymphocyte Blastogenesis by C3c and C3d," J. Immunol. 122(3):1126–1133 (1979).

Servis et al., "C3 Synthetic Peptides Support Growth of Human CR2–Positive Lymphoblastoid B Cells," J. Immunol. 142(7):2207–2212 (1989).

Smith et al., "Comparison of Biosequences," Adv. Appl. Math 2:482–489 (1981).

Smith et al., "Constructed Mutants Using Synthetic Oligodeoxyribonucleotides as Site–Specific Mutagens," Genetics Engineering: Principles and Methods 3:1–32(1981).

Spring et al., "Issues Related to Development of EpsteinBarr Virus Vaccines," J. Natl. Cancer Institute 88(20):1436–1441 (1996).

Tanner et al., "Epstein–Barr Virus gp350/220 Binding to the B Lymphocyte C3d Receptor Mediates Adsorption, Capping, and Endocytosis," Cell 50:203–113 (1987).

Tijssen, "Laboratory Techniques in Biochemistry and Molecular Biology: Practice and Theory of Enzyme Immunoassays," Table of Contents and Chapters 1, 2, 14, and 15 (1985).

Tosato et al., "Epstein–Barr Virus Infection and Immunoregulation in Man," Advance in Immunology, 37:99–149 (F.J. Dixon ed., 1985).

Tsokos et al., "Monovalent Ligands of Complement Receptor 2 Inhibit Whereas Polyvalent Ligands Enhance Anti–Ig-Induced Human B Cell Intracytoplasmic Free Calcium Concentration," J. Immunol. 144(5):1640–1645 (1990).

Walder et al., "Oligodeoxynucleotide–directed mutagenesis using the yeast transformation system," Gene 42:133–139 (1986).

Wong, "Chemistry of Protein Conjugates and Crosslinking," Table of Contents (1991).

* cited by examiner

FIG. 1

AMINO ACID SEQUENCE OF EPSTEIN-BARR VIRUS Gp350/220
Beisel et al., J. Virol. 54, 665-674 (1985)
Translated from GENBANK accession number M10593

FIG. 1A

Epstein-Barr virus major outer envelope glycoprotein Gp350.

SEQ ID NO:1
```
  1 meaallvcqy tiqslihltg edpgffnvei pefpfyptcn vctadvnvti nfdvggkkhq
 61 ldldfgqltp htkavyqprg afggsenatn lfllellgag elaltmrskk lpinvttgee
121 qqvslesvdv yfqdvfgtmw chhaemqnpv ylipetvpyi kwdncnstni tavvraqgld
181 vtlplslpts aqdsnfsvkt emlgneidie cimedgeisq vlpgdnkfni tcsgyeshvp
241 sggiltstsp vatpipgtgy ayslrltprp vsrflgnnsi lyvfysgngp kasggdyciq
301 snivfsdeip asqdmptntt dityvgdnat ysvpmvtsed anspnvtvta fwawpnntet
361 dfkckwtlts gtpsgcenis gafasnrtfd itvsglgtap ktliitrtat nattthkvi
421 fskapesttt sptlnttgfa dpntttglps sthvptnlta pastGptvst advtsptpag
481 ttsgaspvtp spspwdngte skapdmtsst spvttptpna tsptpavttp tpnatsptpa
541 vttptpnats ptlgktspts avttptpnat sptlgktspt savttptpna tsptlgktsp
601 tsavttptpn atGptvgets pqanatnhtl ggtsptpvvt sqpknatsav ttgqhnitss
661 stssmslrps snpetlspst sdnstshmpl ltsahptgge nitqvtpasi sthhvstssp
721 eprpgttsqa sGpgnsstst kpgevnvtkg tppqnatspq apsgqktavp tvtstggkan
781 sttggkhttg hgartstept tdyggdsttp rprynattyl ppstssklrp rwtftsppvt
841 taqatvpvpp tsqprfsnls mlvlqwasla vltlllllvm adcafrrnls tshtyttppy
901 ddaetyv
```

FIG. 1B

Epstein-Barr virus major outer envelope glycoprotein Gp220.

SEQ ID NO:2
```
  1 meaallvcqy tiqslihltg edpgffnvei pefpfyptcn vctadvnvti nfdvggkkhq
 61 ldldfgqltp htkavyqprg afggsenatn lfllellgag elaltmrskk lpinvttgee
121 qqvslesvdv yfqdvfgtmw chhaemqnpv ylipetvpyi kwdncnstni tavvraqgld
181 vtlplslpts aqdsnfsvkt emlgneidie cimedgeisq vlpgdnkfni tcsgyeshvp
241 sggiltstsp vatpipgtgy ayslrltprp vsrflgnnsi lyvfysgngp kasggdyciq
301 snivfsdeip asqdmptntt dityvgdnat ysvpmvtsed anspnvtvta fwawpnntet
361 dfkckwtlts gtpsgcenis gafasnrtfd itvsglgtap ktliitrtat nattthkvi
421 fskapesttt sptlnttgfa dpntttglps sthvptnlta pastGptvst advtsptpag
481 ttsgaspvtp spspwdngte stppqnatsp qapsgqktav ptvtstggka nsttggkhtt
541 ghgartstep ttdyggdstt prprynatty lppstsssklr prwtftsppv ttaqatvpvp
601 ptsqprfsnl smlvlqwasl avltlllllv madcafrrnl stshtyttpp yddaetyv
```

ENHANCEMENT OF B CELL ACTIVATION AND IMMUNOGLOBULIN SECRETION BY CO-STIMULATION OF RECEPTORS FOR ANTIGEN AND EBV GP350/220

RELATED APPLICATION

This application is related to U.S. Provisional Application Ser. No. 60/089,158, filed Jun. 12, 1998, which is hereby incorporated by reference.

GOVERNMENT INTEREST

The invention described herein may be manufactured, licensed and used for governmental purposes without the payment of any royalties to us thereon.

FIELD OF THE INVENTION

The present invention relates to the use of Epstein Barr Virus glycoprotein 350/220 (Gp350/220), and naturally-occurring or synthetically-derived fragments of Gp350/220 which retain the ability to bind to the CR2 receptor on B cells. The invention also relates to non-complement derived peptides that bind to the CR2 receptor as well complement-derived peptides and the hexapeptide LYNVEA. These proteins, peptides, and fragments can be used as vaccine adjuvants and as adjuvanting components of immunostimulatory compositions and vaccines. The invention also relates to the use of non-complement derived peptides that bind to the CR2 receptors, as well as complement derived peptides and the hexapeptide LYNVEA.

BACKGROUND

Complement is the name given to a series of some 20 proteins which are activated by microbial invasion to form an important line of defense against infection. The most well-recognized complement functions are those leading to the osmotic lysis and/or phagocytosis of invading bacteria or parasites. Components in the cell walls of infectious organisms trigger the complex and interconnected pathways of the complement enzyme cascade. During this process the most abundant component, C3, is converted into an enzymatically active form and ultimately cleaved into a number of fragments such as C3a and a series of phagocytosis-promoting peptides including C3b and related peptides, iC3b, C3dg.

C3a is an anaphylatoxin which triggers mast cells and basophils to release a host of chemotactic and inflammatory factors which both contribute to the activation of neutrophils and other phagocytic cells, and concentrate these cells at the site of microbial infection. C3b becomes covalently linked to the surface of the invading organism. The bound C3b interacts with the CR1 (CD35) receptors on the surface of the phagocytic cells. This interaction induces the activated phagocytes to engulf the microbes, which are then fused with cytoplasmic granules and destroyed. The destruction of invading microorganisms by phagocytic cells is an important part of cellular immunity.

More than two decades ago, researchers found that C3 peptides can stimulate resting B cells, thus suggesting that this complement component may also play a role in the humoral immune system. Hartmann, Transplant. Rev. 23:70–104 (1975); and Hartman and Bokisch, J. Exp. Med. 142:600–610 (1975). It is now recognized that these stimulated B cells produce antibacterial antibodies that assist with the process of phagocytosis. Phagocytes are most effective in combating bacteria when the bacteria are coated with antibodies. This effect, termed opsonization, is particularly important in combating encapsulated bacteria which are generally resistant to phagocytosis. It has been suggested that the generation of opsonizing antibodies is favored by the association of bacterial surface antigens with C3 peptides. In other words, the association of C3 on the bacterial surface stimulates B cells to produce anti-bacterial antibodies. Thus, C3 not only stimulates phagocytosis directly, but also stimulates B cells to produce antibodies that bind to the invading microorganism and further promote phagocytosis.

The B cell stimulatory property of the C3 peptides does not require the entire molecule, but is contained in a short sequence containing the hexapeptide LYNVEA. Lambris et al., Proc. Natl. Acad. Sci. USA, 82:4235–39 (1985); and Frade et al., BBRC 188:833–42 (1992) (Incorporated by reference). Notably, C3 molecules, and shorter peptides containing the hexapeptide sequence are only stimulatory as multimers, indicating that cross-linking of the C3 receptor is necessary for B cell proliferation. Servis and Lambris, J. Immunol. 142:2207–12 (1989); and Tsokos et al., J. Immunol. 144:1640–45 (1990). Because many molecules of C3 can bind to a single bacterium, this condition is easily satisfied in vivo.

More recent work indicates that the immunostimulatory effect of cross-linking the C3 receptor on the B cell is mediated by lowering the activation threshold for stimulation of the antigen receptor. When the C3 receptor is cross-linked, either less antigen or antigen with a lower affinity for the antigen receptor on a B cell is required for B cell stimulation. Mongini et al., J. Immunol. 159:3782–91 (1997).

Both B cells and phagocytic cells express CR1 receptors on their cell surface. However, unlike phagocytes, B cells also express the structurally related CR2 receptors (CD21). Cross-linking of CR2 molecules on the B cell surface appears to be directly responsible for the stimulatory effect of C3d, C3dg, C3bi and iC3b peptides. Reviewed in Frade, Seminars in Immunology 2:159–64 (1990). Moreover, CR1, CR2, and another protein, CD19, appear to be associated on the B cell surface. Agents which cross-link any member of this complex result in an enhanced B cell response. This signal may be provided by multimeric C3 peptides, or by antibodies directed against one or more of these associated proteins. Nemerow et al., J. Immunol. 135:3068–73 (1985); and Kozono et al., J. Immunol. 160:1565–72 (1998); Carter and Fearson, Science 256:105–07 (1992).

Indications that crosslinking of CR2 molecules promotes B cell activation have led to the use of C3d sequences as an adjuvant. Dempsey and coworkers demonstrated that a recombinant fusion protein of hen egg lysozyme containing one copy of C3d did not appreciably change the immunogenicity of the lysozyme. However, the fusion of two or three copies of the C3d peptide increased the level of anti-lysozyme antibodies by 1000- and 10,000-fold, respectively. Dempsey et al., Science, 271:348–50 (1996).

In addition to binding complement components, the CR2 receptor has also been identified as the receptor for the B-cell lymphotropic Epstein-Barr Virus (EBV). Fingeroth et al., Proc. Natl. Acad. Sci. USA 81:4510–14 (1984); and Frade et al., Proc. Natl. Acad. Sci. USA 82:1490–93 (1985). EBV has long been recognized as a B cell mitogen and polyclonal activator of antibody synthesis. In vivo, primary EBV infection is characterized by non-specific hypergammaglobulinemia. In vitro, EBV transformed B cells secrete Ig. See review, Giovana and Blaese, Adv. Immunol. 37:99–149 (F. J. Dixon ed., 1985) (Incorporated by reference).

EBV infects over 95% of the world population and is best known as the causative agent for infectious mononucleosis. Moreover, EBV is also strongly associated with a host of pathologies including endemic Burkit's lymphoma, undifferentiated nasopharyngeal carcinoma, X-linked proliferative disorder (XLPD), hairy cell leukemia, post-transplant lymphoproliferative disorders, and some types of Hodgkin's lymphoma, T cell lymphomas, and gastric carcinomas. In addition, unusual EBV-derived tumors are frequently found in immunosuppressed patients, including those infected with the AIDs virus. Consequently, investigators have long sought a safe and effective vaccine to prevent EBV infection. The EBV infection process is initiated by the binding of the major EBV outer membrane glycoprotein, Gp350/220, to CR2. This interaction stimulates phagocytosis or fusion of the virus with the B cell membrane which allows the viral genome to enter the cytoplasm. Tanner et al., Cell 50:2–3–213 (1987). Interestingly, some evidence suggests that C3d and Gp350/220 bind to different sites on the CR2 receptor. Barel et al., J. Immunol. 141:1590–1595 (1988). Viral entry is via the Gp350/220 protein and most of these vaccines have focused on blocking the infection process by eliciting anti-Gp350/220 antibodies. See reviews, Morgan, Vaccine, 10:563–571 (1992); and Spring et al., J. Natl. Cancer Ctr. 88:1436–41 (1996). Of course, these vaccines are designed solely to elicit antibodies against Gp350/220.

Thus, there remains a need for safe and effective adjuvants directed at activating B cells through the CR2 receptor complex.

SUMMARY OF THE INVENTION

The present invention addresses these needs by providing vaccine adjuvants which bind to the CR2 complex. These adjuvants include an Epstein Barr Virus glycoprotein 350/220 or naturally occurring variant thereof, a fusion protein comprising EBV 350/220 sequence sufficient to bind the CR2 receptor, or a recombinant or synthetically-derived fragment of Gp350/220 which retains the ability to bind to the CR2 receptor. The adjuvants of the invention also include non-complement derived peptides that bind to the CR2 receptor as well as complement derived peptides and those related to the hexapeptide LYNVEA. Co-administration of the adjuvant with an antigen of interest, which is other than an antigen comprising EBV 350/220 sequence, enhances the immunogenicity of the antigen. In a preferred embodiment, the adjuvant is directly or indirectly covalently bound to an antigen of interest, to form an immunogenic composition. In a preferred embodiment of the composition, antibodies are elicited against at least one Gp350/220 epitope and against at least one epitope of the antigen.

BRIEF DESCRIPTION OF THE DRAWINGS

FIG. 1 FIG. 1 illustrates the Epstein-Barr virus major outer envelope glycoprotein Gp350/220. Panels 1A and 1B show the sequence of Gp350 and Gp220, respectively.

DETAILED DESCRIPTION OF THE INVENTION

Figure 2:
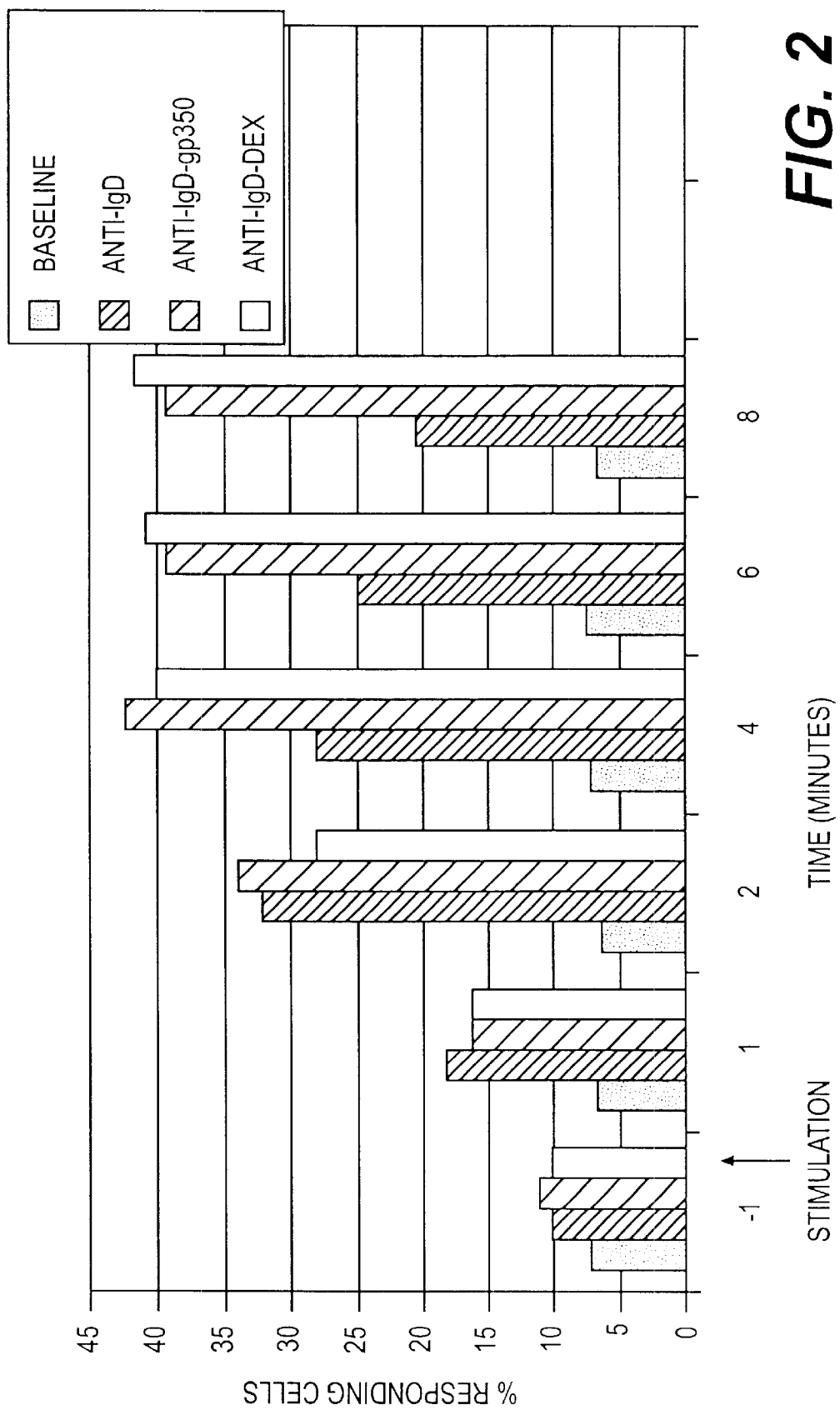
FIG. 2 FIG. 2 illustrates the percentage of purified peripheral B cells responding to anti-IgD, anti-IgD-Gp350 and anti-IgD-dextran.

The present invention addresses the need in the art for safe and effective adjuvants, immunogenic compositions, and vaccines by recognizing the adjuvanting effects of Gp350/220. Prior uses of the protein focused solely on the generation of anti-Gp350/220 antibodies and failed to extend beyond this use. Thus, although EBV infection appears to be a non-specific activator of B cells, the present invention targets that stimulatory effect to antigen-specific B cells by coupling the B cell activating activity of EBV Gp350/220 to one or more copies of an antigen of interest. Using such a composition, a B cell that bears surface Ig specific for the antigen may be simultaneously stimulated through the antigen receptor and through Gp350/220-mediated cross-linking of the CR2 receptor. This co-stimulation will result in the increased production of antibodies specific for the antigen of interest. Thus, this invention presents Gp350/220 as an adjuvant for the generation, stimulation, or enhancement of antigen specific immune responses or as an adjuvanting component of an immunostimulatory composition.

In one embodiment of this invention, one or more moieties comprising at least one antigenic epitope other than Gp350/220 are directly or indirectly conjugated to EBV Gp350/220. Preferably, the moiety is incorporated into an existing EBV vaccine. Antibodies are thus raised against both the EBV Gp350/220 component and against at least one additional epitope of the moiety. In the course of EBV infection, it is likely that multiple copies of Gp350/220 in the viral membrane cross-link CR2 receptors on the B cell surface. Thus, in a preferred embodiment, the Gp350/220 component contains multiple copies of Gp350/220 sequence to promote CR2 cross-linking.

In another embodiment, at least one copy of Gp350/220 is directly or indirectly conjugated to a moiety containing at least one antigenic epitope. In a preferred embodiment, two or more copies of Gp350/220 are directly or indirectly conjugated to the moiety. It is also preferred that the moiety or moieties present multiple copies of at least one antigenic epitope. In each case, the Gp350/220 sequences function as an adjuvant to increase the immunogenicity of the moiety. A moiety may be any antigenic component including haptens, T cell-dependent (TD) antigens, Type 2 T cell-independent (TI-2) antigens, the definitions of which are well known in the art and are described in Roit, *Essential Immunology*, (1994) Blackwell Scientific Publications; and Paul, *Fundamental Immunology*, (1989) Raven Press, both of which are incorporated herein by reference, in their entirety.

A moiety may be a simple chemical compound; a polysaccharide, including bacterial polysaccharides; a naturally occurring, recombinant, or synthetic protein, polypeptide, or peptide; a synthetic peptide; a recombinant fusion protein; or a chemical or enzymatic fragment of any of the preceding. A moiety may include epitopes specific for other EBV antigens. In a preferred embodiment, the moieties are not specific to EBV but elicit antibodies against other infectious diseases, allergens, tumor antigens, or conditions which respond to immune stimulation.

It is well established that multi-epitope antigens are more stimulatory than univalent antigens. This increased immunogenicity appears to result from the ability of multivalent antigens to promote more effective cross-linking of the antigen receptor. Thus, for the purpose of this invention, it is highly preferred that the moiety, or antigen of interest, either contain multiple copies of an antigenic epitope, or be presented as part of a larger construct containing multiple copies of the antigen. For in vitro use, the multi-epitopic moiety may be an antigen analog, such as anti-IgD or anti-IgM coupled to dextran, first described in Brunswick et al., J. Immunol 140:3364 (1988).

In one embodiment, at least one, and preferably two or more copies of Gp350/220 are conjugated to a polysaccharide-TD antigen composition such as those described in W.E. Dick and M. Beurret, Conjugate Vaccines, in *Contrib. Microbiol. Immunol.* Vol.10, pp. 48–114, (J. M. Cruse & R. E. Lewis Jr. eds., 1989), or to any of dual conjugate compositions of Lees et al., Vaccine 1160–66 (1994); U.S. Pat. No. 5,585,100 (Mond and Lees); and U.S. patent application. No. 08/468,359, filed Jun. 6, 1995 (Mond and Lees), each of which is incorporated herein by reference.

The necessary sequence for CR2 binding is contained within the amino acid sequence of the EBV envelope glycoprotein Gp350 (also known as Gp340) and the related splice variant Gp220 (Beisel et al., J. Virol. 54, 665–674 (1985)), examples of which are presented herein as FIGS. 1A and 1B, respectively. Additional sequences are known in the art.

For the purpose of this invention, Gp350/220 further refers to non-complement derived peptides or other molecules which bind to CR2, block the binding of EBV Gp350/220 to CR2, or both. Preferably, Gp350/220 refers to any polypeptide sequence containing EBV Gp350/220 amino acid sequence, a fragment, variant, derivative, or analog thereof, wherein at least a portion of the Gp350/220, Gp350/220 fragment, variant, derivative, or analog sequence which binds to the human CR2 B cell receptor. Such sequence may be contained in a full length protein, a recombinant or synthetic polypeptide or peptide containing Gp350/220 sequence, a recombinant fusion protein, or a chemical or enzymatically-derived fragment of any of the preceding. Although the CR2 binding regions of Gp350/220 have not been investigated, such identification may be made by those of ordinary skill in the art. In addition, portions of the Gp350/220 protein between amino acids 21–26, or between amino acids 372–378, have been suggested to contain sequences necessary for CR2 binding. Tanner et al., Cell 203–213 (1987); and Nemerow et al., 61:1416–20 (1987).

A Gp350/220 polypeptide "variant" as referred to herein means a naturally-occurring or synthetically programmed polypeptide substantially identical to either the Gp350 or Gp220 polypeptides (e.g., SEQ ID Nos: 1 and 2), but which has an amino acid sequence different from that of Gp350 or Gp220 because of one or more deletions, insertions or substitutions. Some Gp350/220 variant sequences have already been identified by sequencing the DNA of different strains of EBV, and are readily available to one of ordinary skill in the art. The variant amino acid sequence preferably is at least 60%, 65%, 70%, or 80%, identical to a Gp350/220 polypeptide amino acid sequence of SEQ ID Nos: 1 or 2, more preferably at least 85% identical, still more preferably at least 90% identical, and most preferably at least 95% identical. The percent identity can be determined, for example, by comparing sequence information using the GAP computer program, version 6.0 described by Devereux et al. (Nucl. Acids Res. 12:387, 1984) and available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math 2:482, 1981). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353–358, 1979; (2) a penalty of 3.0 for each gap and an additional 0.10 penalty for each symbol in each gap; and (3) no penalty for end gaps.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring Gp350/220 variants are also encompassed by the invention. Examples of such variants are proteins that result from alternate mRNA splicing events, from proteolytic cleavage of the Gp350/220 polypeptides, and allelic variants of Gp350/220 polypeptide. Variations attributable to proteolysis include, for example, differences in the N- or C-termini upon expression in different types of host cells, due to proteolytic removal of one or more terminal amino acids from the Gp350/220 polypeptides.

Variants and derivatives of Gp350/220 polypeptides can be obtained by mutation of nucleotide sequences encoding Gp350/220 polypeptides. Alterations of the amino acid sequence can occur naturally, or be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (Gene 42:133, 1986); Bauer et al. (Gene 37:73, 1985); Craik, (BioTechniques, Jan. 12–19, 1985); Smith et al. (Genetic Engineering: Principles and Methods, Plenum Press, 1981); Kunkel (Proc. Natl. Acad. Sci. USA 82:488, 1985); Kunkel et al. (Methods in Enzymol. 154:367, 1987); and U.S. Pat. Nos. 4,518,584 and 4,737,462, all of which are incorporated by reference.

Gp350/220 polypeptides can be modified to create Gp350/220 polypeptide derivatives by forming covalent or aggregative conjugates with other chemical moieties, such as glycosyl groups, polyethylene glycol (PEG) groups, lipids, phosphate, acetyl groups and the like. Covalent derivatives of Gp350/220 polypeptides can be prepared by linking the chemical moieties to functional groups on Gp350/220 polypeptide amino acid side chains or at the N-terminus or C-terminus of a Gp350/220 polypeptide or the extracellular domain thereof. Other derivatives of Gp350/220 polypeptides within the scope of this invention include covalent or aggregative conjugates of Gp350/220 polypeptides or peptide with other proteins or polypeptides, such as by synthesis in recombinant culture as N-terminal or C-terminal fusions. For example, the conjugate can contain a signal or leader polypeptide sequence (e.g. the α-factor leader of Saccharomyces) at the N-terminus of a Gp350/220 polypeptide. The signal or leader peptide co-translationally or post-translationally directs transfer of the conjugate from its site of synthesis to a site inside or outside of the cell membrane or cell wall. Gp350/220 polypeptide conjugates can comprise peptides added to facilitate purification and identification of Gp350/220 polypeptides. Such peptides include, for example, poly-His or the antigenic identification peptides described in U.S. Pat. No. 5,011,912 and in Hopp et al., Bio/Technology 6:1204, 1988.

For the purpose of this invention, Gp350/220 also refers to Gp350/220 analogs which are defined as CR2-binding molecules other than antibodies or portions of complement C3. Such molecules may be selected from naturally-occuring proteins or be totally synthetic. One of skill in the art recognizes that numerous methods are available for selecting molecules which bind to a known receptor. For example, purified or recombinant CR2 could be used as a probe to detect binding in a phage expression library. Clones expressing a protein which binds to CR2 could be isolated and sequenced. Any clones which do not correspond to C3 products would be selected and tested for B cell stimulatory properties. Alternatively, additional naturally-occurring or synthetic sequences which bind CR2 may be selected by functional selection method of Menzel et al., U.S. Pat. No. 5,521,066 (Incorporated herein by reference).

In addition, Gp350/220 analogs may be obtained using the principles of rational drug design. Such a design would comprise the steps of determining the three-dimensional structure of that portion of the CR2 polypeptide which binds to Gp350/220, analyzing the three-dimensional structure for the likely binding site of Gp350/220 or the C3b peptide, synthesizing a molecule that is predicted to bind to a predictive reactive site, and determining the binding and adjuvanting activating activity of the molecule.

Epstein-Barr virus infects over 95% of the world population and is best known as the causative agent for infectious mononucleosis. Moreover, EBV is also strongly associated with a host of pathologies including endemic Burkit's lymphoma, undifferentiated nasopharyngeal carcinoma, X-linked proliferative disorder (XLPD), hairy cell leukemia, post-transplant lymphoproliferative disorders, and some types of Hodgkin's lymphoma, T cell lymphomas, and gastric carcinomas. In addition, unusual EBV-derived tumors are frequently found in immunosuppressed patients, including those infected with the AIDs virus. Consequently, investigators have long sought a safe and effective vaccine to prevent EBV infection. Because viral entry via the Gp350/220 protein is an essential step in viral infection, most of these vaccines have focused on blocking the infection process by eliciting anti-Gp350/220 antibodies. See reviews, Morgan, Vaccine, 10:563–571 (1992); and Spring et al., J. Natl. Cancer Ctr. 88:1436–41 (1996). Of course, these vaccines are designed solely to elicit antibodies against Gp350/220.

The invention also relates peptides that block the binding of the Gp350/220 peptides of the invention. In yet another embodiment, the invention relates to non-complement derived peptides that bind to the CR2 receptor as well as complement-derived peptides and peptides based on the hexapeptide LYNVEA, as well fragments, variants, derivatives, and analogs thereof.

The adjuvants and immunogenic compositions may be produced using recombinant techniques. The production and expression of recombinant proteins and fusion proteins is well known in the art and can be carried out using conventional procedures, such as those in Sambrook et al. *Molecular Cloning: A Laboratory Manual*, Vols. 1–3, (2d ed. 1989), Cold Spring Harbor Laboratory Press (Incorporated herein by reference). The production and purification of recombinant Gp350/220 is known in the art. Tanner et al., Cell 203–213 (1987) (Incorporated by reference). Gp350/220 fusion proteins can also be designed by fusing Gp350/220 polypeptides which retain CR2 binding activity to sequences encoding another polypeptide to aid in the purification of the Gp350/220 sequence. An example of such a fusion is a fusion of sequences encoding a Gp350 polypeptide to sequences encoding the product of the malE gene of the pMAL-c2 vector of New England Biolabs, Inc., or to a hexahistidine sequence. Such fusions allow for affinity purification of the fusion protein. In addition, methods for removing the non-Gp350 sequences from the fusion protein after purification are well known in the art. The adjuvant or composition may also be expressed in transgenic plants or plant products. The adjuvant or composition may then be administered orally as part of the plant or plant product, or be purified from the plant or plant product prior to administration.

The invention also encompasses recombinant nucleic acid vectors, such as plasmids and recombinant viral vectors, that direct the expression of Gp350/220 sequences. The construction and expression of recombinant nucleic acid vectors is well known in the art and includes those techniques contained in Sambrook et al. *Molecular Cloning: A Laboratory Manual*, Vols. 1–3, (2d ed. 1989), Cold Spring Harbor Laboratory Press. Such nucleic acid vectors may be contained in a biological vector such as viruses and bacteria, preferably in a non-pathogenic or attenuated microorganism, including attenuated viruses, bacteria, parasites, and virus-like particles. In one embodiment, the nucleic acid vector directs the expression of Gp350/220 in a biological vector, preferably on the surface of a bacterium, or as part of a viral capsid or envelope. Administration of the biological vector to a patient enhances the immune response to bacterial, viral, or parasitic antigens. Alternatively, Gp350/220 may be expressed as a fusion protein along with at least one antigenic moiety. In a preferred embodiment, the fusion protein is expressed on the surface of bacteria, virus, parasite, or particle to allow for effective antigen presentation. Administration of the biological vector to a patient will result in an enhanced immune response to at least one epitope of the moiety. Similarly, plasmid and viral nucleic acid vectors may be used to direct Gp350/220 or Gp350/220 fusion protein expression in yeast or other eukaryotic cells.

In one embodiment, Gp350/220 is expressed on the surface of mammalian tumor cells. These cells are used to elicit antibodies against tumor-specific antigens. In another embodiment, mammalian host cells are programed to express Gp350/220 as fusion protein along with at least one antigenic moiety. The host then elicits an immune response to at least one epitope of the moiety.

The adjuvants of the invention may be co-administered with at least one antigenic moiety. In a preferred embodiment, the adjuvants are preferably conjugated to the antigenic moiety to form an immunogenic (immunostimulatory) composition. The adjuvant or immunogenic composition may also be conjugated to additional immunostimulatory components. These immunostimulatory components, such as immunomodulators and/or cell targeting moieties, may further enhance the immune response. These entities are co-administered, and preferably chemically conjugated to the adjuvant or immunogenic composition. Such entities may include, for example, (1) detoxified lipopolysaccharides or derivatives, (2) muramyl dipeptides, (3) carbohydrates, lipids, and peptides that may interact with cell surface determinants to target the construct to immunologically relevant cells, (4) interleukins, including IL-1, IL-2, IL-3, IL-4, IL-5, GM-CSF, TGF-β and IFN-γ; (5) one or more universal T cell elements (TCE); (6); CD40 ligand; and (7) antibodies that may interact with cell surface components. In one embodiment, the adjuvanting activity or immunogenicity of the composition may be enhanced by the co-administration or conjugation of an adjuvanting lipoprotein, as described in the copending application, incorporated herein by reference: Induction and Enhancement of the Immune Response to Type 2 T Cell-independent Antigens Conjugated to Lipid or Lipid-containing Moieties of Mond and Snapper, filed Mar. 16, 1998 (Serial No. unassigned).

Any form of conjugation is within the scope of this invention. Methods of conjugation are well known to those of ordinary skill in the art, and include the heteroligation techniques of Brunswick et al., J. Immunol., 140:3364 (1988); Wong, S. S., *Chemistry of Protein Conjugates and Crosslinking*, CRC Press, Boston (1991); Brenkeley et al., "Brief Survey of Methods for Preparing Protein Conjugates With Dyes, Haptens and Cross-Linking Agents," *Bioconjugate Chemistry*, 3, No. 1 (January 1992); and Hermanson, G. T. *Bioconjugate Techniques*, Academic Press, San Diego (1 996), each of which are specifically incorporated by reference.

A preferred method of covalent conjugation is via CDAP (1-cyano-4-"dimethylamino"-pyridinium tetrafluoroborate) activation of the polysaccharide, set forth in applications Ser. Nos. 08/482,616, and 08/482,666, filed Jun. 7, 1995, (08/482,616 being now abandoned), which are continuation-in-part applications of application Ser. No. 08/408,717, filed Mar. 22, 1995, and issued Jul. 29, 1997, as U.S. Pat. No. 5,651,971, which is a continuation-in-part of application Ser. No. 08/124,491, filed Sep. 22, 1993, now abandoned, and further set forth in the continuation of application Ser. No. 08/408,717, application Ser. No. 08/456,694, filed Jun. 1, 1995, which issued Dec. 2, 1997 as U.S. Pat. No. 5,693,326, and as further set forth in the continuation-in-part of application Ser. No. 08/124,491, application Ser. No. 08/124,491, filed Sep. 22, 1993, the disclosures of which are all specifically incorporated herein by reference.

The adjuvants and immunogenic compositions of the invention may be considered pharmaceutical compositions in that they elicit a biological effect on the immune system. When the pharmaceutical composition of the invention contains antigen and is to be administered to an organism, preferably suspended, dissolved, compounded, or encapsulated, in a pharmaceutically acceptable carrier, vehicle, or diluent, it may be referred to as a vaccine. The adjuvants and immunogenic compositions of the claimed invention may be applied to isolated B cells in vitro as a pharmaceutical composition or administered directly to the patient as a vaccine.

The invention also relates to the treatment of a patient, or for the benefit of a patient, by administration of an adjuvanting amount of the adjuvant together with an antigen, or administration of an immunostimulatory amount of the compositions of the vaccine.

A patient is hereby defined as any person or non-human animal in need of immune stimulation, or to any subject for whom treatment may be beneficial, including humans, and non-human animals. Such non-human animals to be treated include all domesticated and feral vertebrates which contain receptors for EBV Gp350/220, in particular, non-human primates such as tamarins. Notably, mice do not normally express CR2, and therefore do not respond to the adjuvanting effect of Gp350/220. However, the creation of transgenic mice which express CR2 on their B cells is within the skill of those in the art. Such CR2 transgenic mice would therefore constitute patients for the purpose of this invention. One of skill in the art will, of course, recognize that the choice of antigens will depend on the disease or condition to be vaccinated against in a particular system.

An immunostimulatory amount refers to that amount of vaccine that is able to stimulate the immune response. As used herein, the immune response is defined as a set of biological effects leading to the body's production of immunoglobulins, or antibodies, in response to a foreign entity. Thus, the immune response refers to the activation of B cells, in vivo or in culture, through stimulation of B cell surface Ig receptor molecules. The measurement of the immune response is within the ordinary skill of those in this art and includes the determination of antibody levels using methods described in the series by P. Tijssen, *Laboratory Techniques in Biochemistry and Molecular Biology: Practice and Theory of Enzyme Immunoassays*, (Burdon & van Knippenberg eds., 3rd ed.,1985) Elsevier, New York; and *Antibodies: A Laboratory Manual*, (Harlow & Lane eds., 1988), Cold Spring Harbor Laboratory Press; as well as procedures such as countercurrent immuno-electrophoresis (GIEP), radioimmunoassay, radio-immunoprecipitation, enzyme-linked immuno-sorbent assays (ELISA), dot blot assays, and sandwich assays, see U.S. Pat. Nos. 4,376,110 and 4,486,530, all of which are incorporated by reference. Measurement of the immune response also includes detection or determination of B cell activation events that may precede antibody production, or signal an increase in antibody production. Such measurements include, B cell proliferation assays, phosphorylation assays, assays of intracytoplasmic free calcium concentration, and other methods of determining B cell activation known in the art. Representative assays are provided in Mongini et al., J. Immunol. 159:3782–91 (1997); Frade, et al., BBRC 188:833–842 (1992); Tsokos et al., J. Immunol. 144:1640–1645 (1990); Delcayre et al., BBRC 159:1213–1220 (1989); and Nemerow et al., J. Immunol. 135:3068–73 (1985) each of which is incorporated by reference.

The practice of the invention includes promoting, enhancing or stimulating an immune response. These actions refer to establishing an immune response that did not previously exist; to optimizing or increasing a desired immune response; to establishing or increasing a secondary response characterized by increased isotype switching, memory response, or both; to providing a statistically increased immunoprotective effect against a pathogen; to generating an equivalent or greater humoral immune response, or other measure of B cell activation, from a reduced or limiting dose of antigen; to generating an increased humoral immune response, or other measure of B cell activation, in response to an equivalent dose of antigen; or to lowering the affinity threshold for B cell activation in vivo or in vitro.

Preferably, an immunostimulatory amount refers to that amount of vaccine that is able to stimulate an immune response in a patient which is sufficient to prevent, ameliorate, or otherwise treat a disease or condition. Similarly, an adjuvanting amount is that amount of adjuvant which, when administered with an antigen, enhances the specific immune response to the antigen. Treatment may be defined as promoting, enhancing, or stimulating an immune response against a moiety or antigen in a patient, or for the benefit of a patient. Such treatment may be for any purpose including experimental, prophylactic, or ameliorative.

Treatment comprises administering the pharmaceutical composition by any method familiar to those of ordinary skill in the art, including intravenous, intraperitoneal, intracorporeal injection, intra-articular, intraventricular, intrathecal, intratonsillar, intramuscular, subcutaneous, topically, intranasally, intravaginally, or orally. The preferred methods of administration are intravenous, intramuscular, intranasal, oral, and subcutaneous injections. The composition may also be given locally, such as by injection into the particular area, either intramuscularly or subcutaneously. The immunological composition may be administered in a slow-release form such as slow-release capsules, pellets, osmotic delivery devices, or pumps.

Secondary booster immunizations may be given at intervals ranging from one week to many months later. The dosage of the primary and secondary inocula can be readily determined by those of ordinary skill in the art, but an acceptable range is 0.01 μg to 100 μg per inoculum.

Any pharmaceutically acceptable carrier can be employed for administration of the composition or vaccine of the invention. Carriers can be solids, powders or liquids, such as water, oils, including petroleum oil, animal oil, vegetable oil, peanut oil, soybean oil, mineral oil, sesame oil, and the like. With intravenous administration, sterile isotonic aqueous solutions are preferred carriers. Saline solutions, aqueous dextrose, and glycerol solutions can also be employed as liquid carriers, particularly for injectable solutions. Suitable pharmaceutical carriers are described in *Remington's Pharmaceutical Sciences*, 18th Edition (A. Gennaro, ed., Mack Pub., Easton, Pa., 1990), incorporated by reference.

The immunological composition may also be formulated with solubilizing agents, emulsifiers, stabilizers, flavorants, and other components, including adjuvants. An adjuvant is herein defined as any composition which, when combined with an antigen, enhances the specific immune response to the antigen. Common adjuvants include alum, Freund's, Titermax (CytRyx Corp.), RIBI T-700 adjuvant (RIBI Immunochemical), and STIMULON adjuvant QS 21 (Aquila Biopharm.).

The CR2 stimulatory activity of Gp350/220 sequences may be substituted with other molecules that bind to CR2 or to CR2-associated proteins such as CR1 and CD19. Specifically, these include: complement C3d, C3dg, C3bi, iC3b, and peptides thereof which contain the hexapeptide LYNVEA and bind to CR2, as well as antibodies directed against CR1, CR2, or CD19. However, the use of autologous sequences in a vaccine raises the possibility of eliciting an autoimmune response.

This scenario is of particular concern where the endogenous protein is highly stimulatory to B cells. Although the immune system normally (and necessarily) recognizes complement components as "self" antigens, the conjugation or fusion of C3d, or related peptides, to a foreign antigen presents this protein in an unusual context. Moreover, such constructs may display C3d epitopes that are rarely encountered in a natural setting. Indeed, elicitation of an autoimmune response against complement components may be particularly favored because multiple copies of these molecules are required to elicit an adjuvanting response, and this arrangement is not found in nature. In any event, presenting a host with an altered form of C3d raises the very real possibility of breaking tolerance to C3d and thereby inducing antibodies to a plethora of complement components derived from C3. As is readily appreciated by those in the art, the generation of antibodies against complement could result serious autoimmune pathologies.

In contrast, Gp350/220 sequences are highly preferred as adjuvants and adjuvanting components of immunostimulatory compositions, as compared to complement components, for the following additional reasons:

1) Antibodies raised against epitopes of the Gp350/220 adjuvant may themselves be beneficial in providing protection against EBV infection or infectivity.

2) Where the antigen linked to the complement component is of low molecular weight, the resulting construct would be of low molecular weight as well. The in vivo half-life of low molecular weight constructs is often short and this rapid elimination detracts from immunogenicity. In contrast, compositions based on the larger Gp350/220 polypeptides will be expected to have a longer effective half-life than those based on C3d.

3) Effective antigen presentation depends on cross-linking of the antigen receptors on a B cell. Because more copies of antigen can be ligated to the larger Gp350/220 proteins than to C3b, constructs based on Gp350/220 will be more antigenic.

4) Antibodies raised against CR1, CR2, or CD19 are expensive and difficult to produce. Moreover, vaccination with antibody sequences can elicit undesirable immune responses, including autoimmune reactions.

5) The safety and efficacy of Gp350/220 vaccine components has already been examined, whereas the toxicity of C3 components is uncertain. Because complement activation triggers the acute inflammatory response, it is possible that complement-based adjuvants will stimulate inflammation.

6) It has been suggested in the field that C3d-fusion proteins are difficult to synthesize and purify, possibly due to problems in folding recombinantly produced C3d polypeptides.

7) Proper folding of C3d is critical to CR2 binding. In genetically engineered constructs with antigen, there may be antigens that distort the folding of C3d and reduce or eliminate its binding to the receptor. In contrast, folding of the CR2-binding domain in the larger Gp350/220 proteins is less likely to be disrupted by fusion with antigen.

The present invention is illustrated by the following Examples, which are not intended to be limiting in any way.

EXAMPLE 1

Preparation of Conjugates and Controls

Reagents

Purified recombinant EBV Gp350 and Respiratory Syncitial Virus (RSV) glycoprotein FG were obtained from SmithKline Beecham Biologicals at 538 μg/ml and 319 μg/ml respectively. These proteins were then concentrated using a FILTRON Microsep concentrator to 1 mg/ml and 0.8 mg/ml, respectively. 5XHE is 75 mM HEPES, 10 mM EDTA, pH 7.3. SATA (N-hydroxysuccinimidyl S-acetylthioacetate from BioAffinity Systems), was prepared as a 10 mM solution in dimethylformamide (DMF). The human IgD-specific monoclonal antibody δIA6.2 (25 mg/ml in 150 mM HEPES, 2 mM EDTA, pH 7.3) was a gift from Dr. John Kearny of the University of Alabama, Birmingham, and is described in Halista et al., Ped. Res. 43:496–503 (1998) (Incorporated by reference). SIA (N-Hydroxysuccinimidyl iodoacetate from BioAffinity Systems) was 10 mM in DMF, except for preparation of anti-Ig-Dex where it was 100 mM in DMF. HEH is 0.5M hydroxylamine in 5XHE.

Gp350 and RSV FG were coupled to anti-IgD antibodies to create anti-IgD-Gp350 and anti-IgD-FG, as generally described in Lees et al., J. Immunol. 145:3594–3600 (1990), incorporated herein by reference. Briefly, 0.5 mg (500 μl) of Gp350 was thiolated by mixing with 50 μl of 10 mM SATA in DMF to generate Gp350-SATA. Similarly, 0.5 mg (625 μl) of FG was added to 25 μl 5XHE and 50 μl of 10 mM SATA in DMF to generate FG-SATA. To iodacetylate the anti-IgD antibody 2 mg (80 μl) of δIA6.2 was added to 13.3 μl of 10 mM Iodoacetamide in water. After 10 minutes, 26 μl of 10 mM SIA in DMF was added to generate δIA6.2-SIA.

Each of the above reactions was allowed to proceed for ~2 hours at RT then dialyzed overnight against 10 mM MES, 150 mM NaCl, 2 mM EDTA, pH 6. The SIA reaction was kept in the dark.

anti-Ig-Gp350 (anti-IgD-Gp350)

169 μl (~0.5 mg) of δIA6.2-SIA was added to 560 μl (~0.5 mg) Gp350-SATA and 80 μl of HEH. The reaction was then concentrated to ~200 μl using a FILTRON Microsep 10 and incubated overnight at 4° C. in the dark. The reaction was then quenched by making 0.2 mM in mercaptoethanol for 1 hour, followed by making 10 mM in iodoacetamide. The conjugate was run over a 1×60 cm S400HR column equilibrated with PBS. The void volume fractions were pooled and sterile filtered through a Millipore 0.2μ Millex filter. The resulting anti-Ig-Gp350 preparation contained less than 5% unconjugated δIA6.2 as determined by HPLC analysis.

anti-Ig-FG (anti-IgD-FG)

169 μl (~0.5 mg) of δIA6.2-SIA was added to 890 μl (~0.5 mg) FG-SATA and 117 μl of HEH. The reaction was then concentrated to ~200 μl using a FILTRON Microsep 10 and incubated overnight at 4° C. in the dark. The reaction was then quenched by making 0.2 mM in mercaptoethanol for 1 hour, followed by making 10 mM in iodoacetamide. The conjugate was run over a 1×60 cm S200HR column equilibrated with PBS. The void volume fractions were pooled and sterile filtered through a Millipore 0.2μ Millex filter. HPLC analysis was used to determine that the anti-Ig-FG preparation contained less than 20% unconjugated δIA6.2.

The protein concentrations of anti-Ig-Gp350 and anti-Ig-FG conjugates were estimated by $OD_{280}$ using 1 mg/ml/ absorbance unit.

anti-Ig control (anti-IgD)

112 μl (~0.33 mg) of δIA6.2-SIA was added to 12.5 μl of HEH. The reaction was incubated overnight at 4° C. The reaction was then quenched by making 0.2 mM in mercaptoethanol for 1 hour, followed by making 10 mM in iodoacetamide. The reaction was then dialyzed against PBS to provide an anti-Ig control. The protein concentrations of the anti-Ig control was estimated by $OD_{280}$ using 0.7 mg/ml/ absorbance unit.

anti-Ig-Dextran (anti-IgD-Dex)

High molecular weight dextran T2000 (Pharmacia) was conjugated to δIA6.2 essentially as described in Lees et al., Vaccine 12:1160–66 (1994); U.S. Pat. No. 5,585,100 (Mond and Lees); and U.S. patent application No. 08/468,359, filed Jun. 6, 1995 (Mond and Lees) (Incorporated by reference). AECM dextran was prepared by the method of Brunswick et al., J. Immunol. 140:3364 (1989) (Incorporated by reference) and fractionated on an S400HR column. The size-fractionated AECM dextran was suspended in saline to 15.5 mg/ml. DEX-SIA was generated by mixing 774 μl of the AECM dextran with 100 μl 5XHE and 100 μl of 100 mM was in DMF. In a separate reaction, 3 mg of δIA6.2 (20 mg/ml in PBS) was mixed with 50 μl of 5XHE and 24 μl of 10 mM SATA in DMF. Each reaction was incubated for ~2 hr at RT then dialyzed overnight against 10 mM sodium acetate, 100 mM NaCl, 2 mM EDTA, pH 5, in the dark.

Approximately 3 mg of the DEX-SIA and about 3 mg of the SATA-treated antibody were combined with 75 μl of 5XHE containing 0.5M hydroxylamine. The reaction was allowed to proceed overnight at 4° in the dark. The reaction was then quenched by making 0.2 mM in mercaptoethanol for 1 hour, followed by making 10 mM in iodoacetamide to consume unreacted thiol groups. Unconjugated protein was removed by gel filtration on a 1×60 cm S400HR column equilibrated with PBS. The void volume fractions are pooled and sterile filtered through a Millipore 0.2μ Millex filter. Protein concentration was determined from $OD_{280}$ using 0.71 mg/ml protein/absorbance unit. Dextran concentration was determined using the resorcinol assay of Monsigny et al., Anal. Chem 175:525 (1988). The protein/dextran ratio of the conjugate was determined to be about 1 mg/mg.

anti-CR2 antibody

Anti-CR2-specific antisera HB5 was a kind gift from Dr. George Tsokos (Uniformed Services University of the Health Sciences, Bethesda, Md.).

EXAMPLE 2

Demonstration of the Adjuvanting Effect of Gp350/220 Sequences

The enhanced immunostimulatory effect obtained by administering the compositions of the invention is demonstrated by the following in vitro model. B cells were purified from human peripheral human blood by standard techniques. The purified B cells were then cultured in microtiter plates at 200,000 cells per well in the presence or absence of various concentrations of Gp350, anti-Ig antibodies, FG, anti-Ig-dextran, or anti-Ig-Gp350 described in Example 1. Tritiated thymidine was added to the culture 48 hours after the presentation of the stimuli. 18 hours following the addition of tritiated thymidine, the cells were harvested and the amount of incorporated tritium was determined by liquid scintillation spectrometry.

Anti-Ig-Gp350 provides an in vitro model for the antigen-containing compositions of the invention wherein cross-linking of membrane bound Ig receptor by the anti-IgD antibodies simulates the cross-linking of Ig receptors by antigen. The RSV viral coat glycoprotein FG conjugated to anti-IgD was used as a control for the presentation of a similarly-sized protein that is not known to bind CR2. The amount of incorporated tritium reflects the proliferative activity of the cells. This in turn, provides a measure of the immunostimulatory effect of the tested compounds.

The data in Table I demonstrate that anti-Ig conjugated to Gp350 stimulated high levels of proliferation even at concentrations as low as 0.01 μg/ml. In contrast, anti-Ig conjugated to glycoprotein FG was not stimulators.

This experiment demonstrates that Gp350/220 provides an excellent carrier for antigens of interest. The Gp350/220 sequences provide an adjuvanting effect which enhances immune responsiveness even at low antigen concentrations.

TABLE 1

ENHANCED STIMULATORY ACTIVITY OF ANTI-Ig CONJUGATED TO Gp350 ON HUMAN B LYMPHOCYTES

| Stimuli | Concentration of Stimuli (μg/ml) | | | | |
|---|---|---|---|---|---|
| | 0 | 10 | 1 | 0.1 | .01 |
| | Thymidine Incorporation (cpm) | | | | |
| (medium) | 1615 | | | | |
| Gp350 | | 3,154 | 1,626 | 2,314 | 2,612 |
| anti-Ig--FG | | 6,196 | 4,353 | 2,238 | ND |
| anti-Ig control | | 2,320 | 2,516 | 2,722 | 2,811 |
| anti-Ig--dextran | | 20,699 | 19,292 | 26,826 | 27,830 |
| anti-Ig-Gp350 | | 19,223 | 19,047 | 20,673 | 20,949 |

EXAMPLE 2

The Adjuvanting Effect of Gp350/220 Sequences is Attenuated by Anti-CR2 Antibodies B cells were purified from human peripheral human blood and cultured in microtiter plates at 200,000 cells per well in the presence or absence of stimuli (anti-Ig-dextran or anti-Ig-Gp350) with or without anti-CR2 antibody HB5. Tritiated thymidine was added to the culture 72 hours after the presentation of the stimuli. 18 hours following the addition of tritiated thymidine, the cells were harvested and the amount of incorporated tritium was determined by liquid scintillation spectrometry.

The data in Table 2 shows that the stimulatory effect of anti-Ig-dextran is enhanced by the addition of antibodies specific for CR2. In contrast, the stimulatory effect of anti-Ig-Gp350 is attenuated by addition of anti-CR2, suggesting that the Gp350 moiety of anti-Ig-Gp350 acts through the CR2 complex.

TABLE 2

ANTIBODIES DIRECTED AGAINST CR2 ATTENUATE THE STIMULATORY ACTIVITY OF ANTI-IgD CONJUGATED TO Gp350

| Stimuli (μg/ml) | Concentration of anti-CR2 antibody (μg/ml) | | | |
|---|---|---|---|---|
| | 0 | 100 | 10 | 1 |
| | Thymidine Incorporation (cpm) | | | |
| (medium) | 915 +/−157 | 184 +/−31 | 318 +/−72 | 468 +/−89 |
| anti-Ig--Gp350 (1) | 8,472 +/−1,228 | 1,013 +/−83 | 1,126 +/−81 | 2,370 +/−16 |
| anti-Ig--Gp350 (10) | 19,759 +/−1,710 | 1,007 +/−547 | 2,606 +/−331 | 7,275 +/−1,362 |
| anti-Ig--dextran (1) | 2,184 +/−262 | 25,706 +/−324 | 14,453 +/−900 | 4,135 +/−76 |
| anti-Ig--dextran (10) | 13,195 +/−1,325 | 16,066 +/−2,485 | 29,325 +/−2,390 | 20,968 +/−1,277 |

EXAMPLE 4

Gp350/220 Sequences Initiate an Extended B Cell Stimulatory Response

The percentage of cells responding to anti-Ig-Gp350 was determined using the indo-1 loading assay as described in Brunswick et al., Proc. Nat'l. Acad. Sci. USA 86:6724–28 (1989) (incorporated by reference). Briefly, B cells, purified from human peripheral human blood, were loaded with indo-1 and stimulated by the addition of anti-Ig, anti-Ig-dex, and anti-Ig-Gp350 to a final concentration of 1.0 ug/ml. Calcium flux was measured and used to calculate the percentage of cells responding to the stimuli.

FIG. 2 shows the percentage of cells responding over the course of the assay. Anti-Ig-Gp350 and anti-Ig-dex both activate approximately 40% of the B cells within four minutes of stimulation. This level remains relatively constant until at least eight minutes post-stimulation (the duration of the assay). In contrast, the stimulatory effect of unconjugated anti-Ig antibodies (anti-IgD) peaks at two minutes after stimulation and declines to 20% by eight minutes.

EXAMPLE 5

Figure 3:
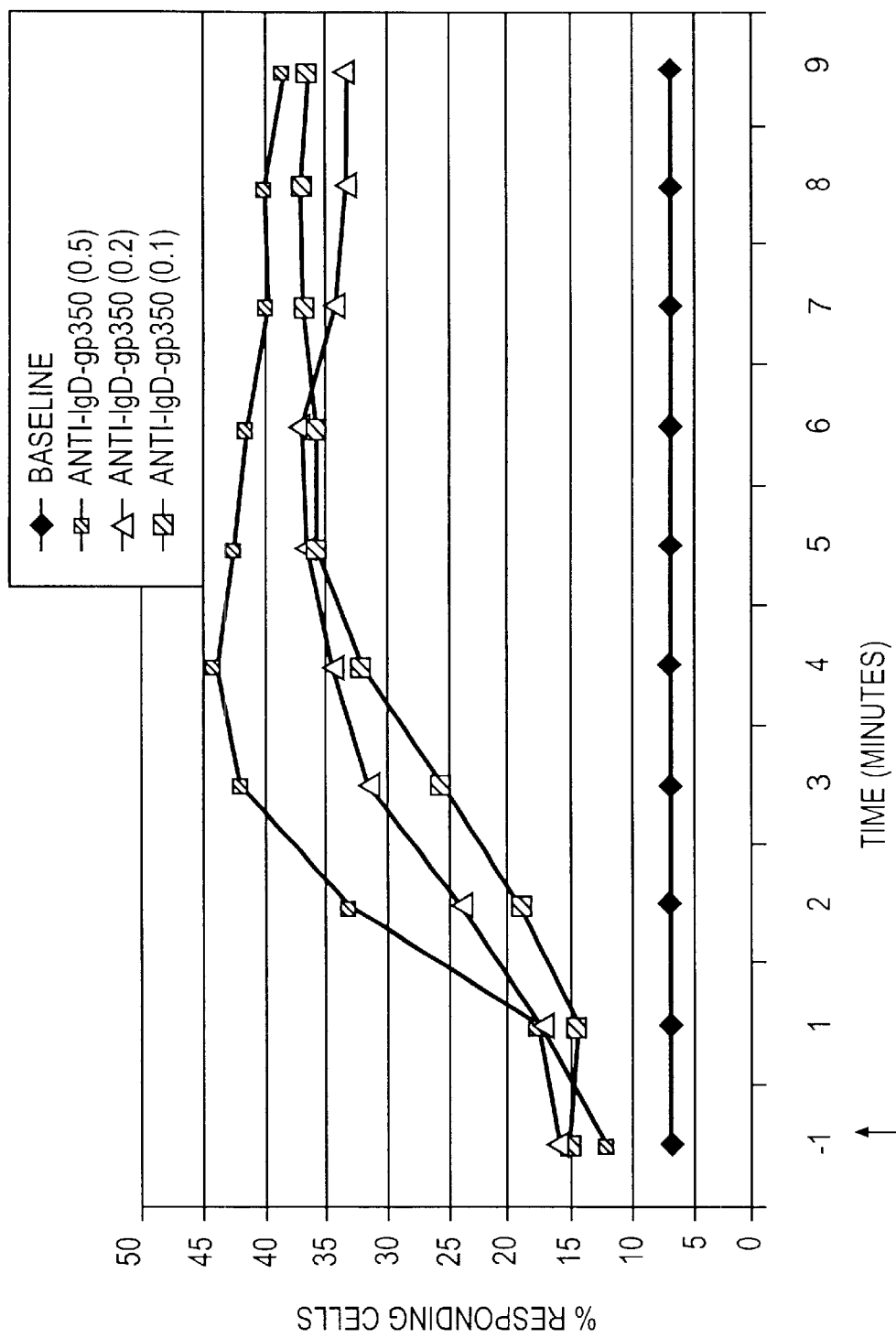
FIG. 3 FIG. 3 illustrates the percentage of purified peripheral B cells responding to various concentrations of anti-IgD-Gp350.

Low Levels of Gp350/220 Sequences are required to Initiate an Extended B Cell Stimulatory Response B cell sensitivity to stimulation by anti-Ig-Gp350 was analyzed using the indo-1 loading assay described in Example 4. Briefly, indo-1 loaded B cells were stimulated with various concentrations of anti-Ig-Gp350 and calcium flux was measured every minute for nine minutes. FIG. 3 shows that as little as 0.1 ug/ml of anti-Ig-Gp350 generates a stable response in about one third of the isolated B cells.

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with a true scope and spirit of the invention being indicated by the following claims.

We claim:

1. A method of treating a patient comprising: administering a composition comprising:

at least one Epstein-Barr virus (EBV) Gp350/220 sequence that binds to a CR2 receptor (CR2) covalently conjugated to at least one protein, peptide, polypeptide, or polysaccharide comprising an antigenic epitope other than an epitope of EBV Gp350/220;

such that said EBV Gp350/220 sequence and said protein, peptide, polypeptide, or polysaccharide are on the same molecule;

wherein the composition promotes a humoral immune response with respect to said antigenic epitope other than an epitope of EBV Gp350/220.

2. The method of claim 1 wherein at least one Gp350/220 sequence comprises amino acids 21–26 of Gp350/220 (SEQ ID NO. 1 or SEQ ID NO. 2).

3. The method of claim 1 wherein at least one Gp350/220 sequence comprises amino acids 372–378 of Gp350/220 (SEQ ID NO. 1 or SEQ ID NO. 2).

4. The method of claim 1 wherein at least one Gp350/220 sequence is a fragment, amino acid variant, or derivative of Gp350/220.

5. The method of claim 1 wherein the composition comprises at least two EBV Gp350/220 sequences that bind to CR2.

6. The method of claim 1 wherein the composition comprises multiple copies of said EBV Gp350/220 sequence that binds to CR2.

7. The method of claim 1 wherein the composition comprises a multiplicity of said protein, peptide, polypeptide, or polysaccharide comprising an antigenic epitope other than an epitope of EBV Gp350/220.

8. The method of claim 1 wherein said protein, peptide, polypeptide, or polysaccharide comprises multiple copies of said antigenic epitope other than an epitope of EBV Gp350/220.

9. The method of claim 1 wherein said protein, peptide, polypeptide, or polysaccharide comprising an antigenic epitope other than an epitope of EBV Gp350/220 is selected from haptens, T cell-dependent antigens, and Type 2 T cell-independent antigens.

10. The method of claim 1 wherein the elicited antibodies are specific for an allergen, a tumor antigen, or an infectious disease other than EBV.

11. The method of claim 1 wherein the composition further elicits antibodies specific for EBV.

12. The method of claim 1 wherein the composition further comprises a pharmaceutically acceptable carrier.

13. The method of claim 1 wherein the conjugation is by CDAP (1-cyano-4-"dimethylamino"-pyridinium tetrafluoroborate) chemistry.

14. The method of claim 1 wherein at least one protein, peptide, polypeptide, or polysaccharide comprising an antigenic epitope other than an epitope of EBV Gp350/220 and at least one EBV Gp350/220 sequence comprise a recombinant fusion protein.

15. The method of claim 1 wherein at least two proteins, peptides, polypeptides, or polysaccharides each comprising an antigenic epitope other than an epitope of EBV Gp350/220 and at least one EBV Gp350/220 sequence comprise a recombinant fusion protein.

16. The method of claim 1 wherein the composition is administered via a biological vector.

17. The method of claim 16 wherein the biological vector is selected from: a plant or plant product; bacterium; parasite; virus or virus-like particle; a yeast, mammalian, or other eukaryotic cell.

18. The method of claim 1 wherein said at least one EBV Gp350/220 sequence is expressed on the surface of a bacterium, viral capsid or envelope, parasite, or mammalian tumor cell.

19. The method of claim 18 wherein the composition enhances the immune response to bacterial, viral, parasitic, or tumor-specific antigens.

20. The method of claim 1 wherein said EBV Gp350/220 sequence is conjugated to said protein, peptide, polypeptide, or polysaccharide such that one or more natural, synthetic, or chemical molecule, spacer, linker, amino acid, polypeptide, protein, hapten, antigen, or polysaccharide intervenes between said EBV Gp350/220 sequence and said protein, peptide, polypeptide, or polysaccharide comprising said antigenic epitope.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 907 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

Met Glu Ala Ala Leu Leu Val Cys Gln Tyr Thr Ile Gln Ser Leu Ile
1            5                  10               15

His Leu Thr Gly Glu Asp Pro Gly Phe Phe Asn Val Glu Ile Pro Glu
            20                  25               30

-continued

```
Phe Pro Phe Tyr Pro Thr Cys Asn Val Cys Thr Ala Asp Val Asn Val
            35                  40                  45

Thr Ile Asn Phe Asp Val Gly Gly Lys Lys His Gln Leu Asp Leu Asp
 50                  55                  60

Phe Gly Gln Leu Thr Pro His Thr Lys Ala Val Tyr Gln Pro Arg Gly
 65                  70                  75                  80

Ala Phe Gly Gly Ser Glu Asn Ala Thr Asn Leu Phe Leu Leu Glu Leu
                 85                  90                  95

Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
            115                 120                 125

Asp Val Tyr Phe Gln Asp Val Phe Gly Thr Met Trp Cys His His Ala
            130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
            195                 200                 205

Ile Glu Cys Ile Met Glu Asp Gly Glu Ile Ser Gln Val Leu Pro Gly
            210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
            275                 280                 285

Gly Pro Lys Ala Ser Gly Gly Asp Tyr Cys Ile Gln Ser Asn Ile Val
            290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
            355                 360                 365

Thr Ser Gly Thr Pro Ser Gly Cys Glu Asn Ile Ser Gly Ala Phe Ala
            370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Leu Asn Thr Gly Phe Ala Asp Pro Asn Thr Thr Thr Gly Leu
            435                 440                 445
```

-continued

```
Pro Ser Ser Thr His Val Pro Thr Asn Leu Thr Ala Pro Ala Ser Thr
    450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Trp Asp
                485                 490                 495

Asn Gly Thr Glu Ser Lys Ala Pro Asp Met Thr Ser Ser Thr Ser Pro
                500                 505                 510

Val Thr Thr Pro Thr Pro Asn Ala Thr Ser Pro Thr Pro Ala Val Thr
        515                 520                 525

Thr Pro Thr Pro Asn Ala Thr Ser Pro Thr Pro Ala Val Thr Thr Pro
        530                 535                 540

Thr Pro Asn Ala Thr Ser Pro Thr Leu Gly Lys Thr Ser Pro Thr Ser
545                 550                 555                 560

Ala Val Thr Thr Pro Thr Pro Asn Ala Thr Ser Pro Thr Leu Gly Lys
                565                 570                 575

Thr Ser Pro Thr Ser Ala Val Thr Thr Pro Thr Pro Asn Ala Thr Ser
                580                 585                 590

Pro Thr Leu Gly Lys Thr Ser Pro Thr Ser Ala Val Thr Thr Pro Thr
        595                 600                 605

Pro Asn Ala Thr Gly Pro Thr Val Gly Glu Thr Ser Pro Gln Ala Asn
        610                 615                 620

Ala Thr Asn His Thr Leu Gly Gly Thr Ser Pro Thr Pro Val Val Thr
625                 630                 635                 640

Ser Gln Pro Lys Asn Ala Thr Ser Ala Val Thr Thr Gly Gln His Asn
                645                 650                 655

Ile Thr Ser Ser Ser Thr Ser Ser Met Ser Leu Arg Pro Ser Ser Asn
                660                 665                 670

Pro Glu Thr Leu Ser Pro Ser Thr Ser Asp Asn Ser Thr Ser His Met
        675                 680                 685

Pro Leu Leu Thr Ser Ala His Pro Thr Gly Gly Glu Asn Ile Thr Gln
        690                 695                 700

Val Thr Pro Ala Ser Ile Ser Thr His His Val Ser Thr Ser Ser Pro
705                 710                 715                 720

Glu Pro Arg Pro Gly Thr Thr Ser Gln Ala Ser Gly Pro Gly Asn Ser
                725                 730                 735

Ser Thr Ser Thr Lys Pro Gly Glu Val Asn Val Thr Lys Gly Thr Pro
                740                 745                 750

Pro Gln Asn Ala Thr Ser Pro Gln Ala Pro Ser Gly Gln Lys Thr Ala
        755                 760                 765

Val Pro Thr Val Thr Ser Thr Gly Gly Lys Ala Asn Ser Thr Thr Gly
770                 775                 780

Gly Lys His Thr Thr Gly His Gly Ala Arg Thr Ser Thr Glu Pro Thr
785                 790                 795                 800

Thr Asp Tyr Gly Gly Asp Ser Thr Thr Pro Arg Pro Arg Tyr Asn Ala
                805                 810                 815

Thr Thr Tyr Leu Pro Pro Ser Thr Ser Ser Lys Leu Arg Pro Arg Trp
                820                 825                 830

Thr Phe Thr Ser Pro Pro Val Thr Thr Ala Gln Ala Thr Val Pro Val
            835                 840                 845

Pro Pro Thr Ser Gln Pro Arg Phe Ser Asn Leu Ser Met Leu Val Leu
        850                 855                 860

Gln Trp Ala Ser Leu Ala Val Leu Thr Leu Leu Leu Leu Leu Val Met
```

```
                865                 870                 875                 880
Ala Asp Cys Ala Phe Arg Arg Asn Leu Ser Thr His Thr Tyr Thr
                            885                 890                 895
Thr Pro Pro Tyr Asp Asp Ala Glu Thr Tyr Val
            900                 905
```

(2) INFORMATION FOR SEQ ID NO:2:

(i) SEQUENCE CHARACTERISTICS:
        (A) LENGTH: 658 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Glu Ala Ala Leu Leu Val Cys Gln Tyr Thr Ile Gln Ser Leu Ile
1               5                   10                  15
His Leu Thr Gly Glu Asp Pro Gly Phe Phe Asn Val Glu Ile Pro Glu
                20                  25                  30
Phe Pro Phe Tyr Pro Thr Cys Asn Val Cys Thr Ala Asp Val Asn Val
            35                  40                  45
Thr Ile Asn Phe Asp Val Gly Lys Lys His Gln Leu Asp Leu Asp
 50                 55                  60
Phe Gly Gln Leu Thr Pro His Thr Lys Ala Val Tyr Gln Pro Arg Gly
65                  70                  75                  80
Ala Phe Gly Gly Ser Glu Asn Ala Thr Asn Leu Phe Leu Leu Glu Leu
                85                  90                  95
Leu Gly Ala Gly Glu Leu Ala Leu Thr Met Arg Ser Lys Lys Leu Pro
            100                 105                 110
Ile Asn Val Thr Thr Gly Glu Glu Gln Gln Val Ser Leu Glu Ser Val
        115                 120                 125
Asp Val Tyr Phe Gln Asp Val Phe Gly Thr Met Trp Cys His His Ala
    130                 135                 140
Glu Met Gln Asn Pro Val Tyr Leu Ile Pro Glu Thr Val Pro Tyr Ile
145                 150                 155                 160
Lys Trp Asp Asn Cys Asn Ser Thr Asn Ile Thr Ala Val Val Arg Ala
                165                 170                 175
Gln Gly Leu Asp Val Thr Leu Pro Leu Ser Leu Pro Thr Ser Ala Gln
            180                 185                 190
Asp Ser Asn Phe Ser Val Lys Thr Glu Met Leu Gly Asn Glu Ile Asp
        195                 200                 205
Ile Glu Cys Ile Met Glu Asp Gly Glu Ile Ser Gln Val Leu Pro Gly
    210                 215                 220
Asp Asn Lys Phe Asn Ile Thr Cys Ser Gly Tyr Glu Ser His Val Pro
225                 230                 235                 240
Ser Gly Gly Ile Leu Thr Ser Thr Ser Pro Val Ala Thr Pro Ile Pro
                245                 250                 255
Gly Thr Gly Tyr Ala Tyr Ser Leu Arg Leu Thr Pro Arg Pro Val Ser
            260                 265                 270
Arg Phe Leu Gly Asn Asn Ser Ile Leu Tyr Val Phe Tyr Ser Gly Asn
        275                 280                 285
Gly Pro Lys Ala Ser Gly Gly Asp Tyr Cys Ile Gln Ser Asn Ile Val
    290                 295                 300
Phe Ser Asp Glu Ile Pro Ala Ser Gln Asp Met Pro Thr Asn Thr Thr
```

-continued

```
305                 310                 315                 320
Asp Ile Thr Tyr Val Gly Asp Asn Ala Thr Tyr Ser Val Pro Met Val
            325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
            355                 360                 365

Thr Ser Gly Thr Pro Ser Gly Cys Glu Asn Ile Ser Gly Ala Phe Ala
            370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
            405                 410                 415

His Lys Val Ile Phe Ser Lys Ala Pro Glu Ser Thr Thr Thr Ser Pro
            420                 425                 430

Thr Leu Asn Thr Thr Gly Phe Ala Asp Pro Asn Thr Thr Thr Gly Leu
            435                 440                 445

Pro Ser Ser Thr His Val Pro Thr Asn Leu Thr Ala Pro Ala Ser Thr
    450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Trp Asp
            485                 490                 495

Asn Gly Thr Glu Ser Thr Pro Pro Gln Asn Ala Thr Ser Pro Gln Ala
            500                 505                 510

Pro Ser Gly Gln Lys Thr Ala Val Pro Thr Val Thr Ser Thr Gly Gly
            515                 520                 525

Lys Ala Asn Ser Thr Thr Gly Gly Lys His Thr Thr Gly His Gly Ala
    530                 535                 540

Arg Thr Ser Thr Glu Pro Thr Thr Asp Tyr Gly Gly Asp Ser Thr Thr
545                 550                 555                 560

Pro Arg Pro Arg Tyr Asn Ala Thr Thr Tyr Leu Pro Pro Ser Thr Ser
            565                 570                 575

Ser Lys Leu Arg Pro Arg Trp Thr Phe Thr Ser Pro Pro Val Thr Thr
            580                 585                 590

Ala Gln Ala Thr Val Pro Val Pro Pro Thr Ser Gln Pro Arg Phe Ser
            595                 600                 605

Asn Leu Ser Met Leu Val Leu Gln Trp Ala Ser Leu Ala Val Leu Thr
            610                 615                 620

Leu Leu Leu Leu Leu Val Met Ala Asp Cys Ala Phe Arg Arg Asn Leu
625                 630                 635                 640

Ser Thr Ser His Thr Tyr Thr Thr Pro Pro Tyr Asp Asp Ala Glu Thr
            645                 650                 655

Tyr Val
```